United States Patent [19]

Escalona

[11] Patent Number: 5,694,942
[45] Date of Patent: Dec. 9, 1997

[54] ANALYSIS OF HEART WAVEFORMS

[75] Inventor: Omar Jacinto Escalona, County Antrim, Northern Ireland

[73] Assignee: British Technology Group Limited, London, England

[21] Appl. No.: 557,040

[22] PCT Filed: May 20, 1994

[86] PCT No.: PCT/GB94/01117

§ 371 Date: Jan. 30, 1996

§ 102(e) Date: Jan. 30, 1996

[87] PCT Pub. No.: WO94/28494

PCT Pub. Date: Dec. 8, 1994

[30] Foreign Application Priority Data

May 21, 1993 [GB] United Kingdom .................. 9310604

[51] Int. Cl.$^6$ ............................................... A61B 5/0452
[52] U.S. Cl. ............................................... 128/699
[58] Field of Search ...................... 364/413.06; 128/696, 128/699, 702, 703, 704, 708, 705

[56] References Cited

U.S. PATENT DOCUMENTS 5,341,811  8/1994  Cano ......................................... 128/696

OTHER PUBLICATIONS

G. Breithardt et al, "Standards for analysis of ventricular late potentials using high resolution or signal–averaged electrocardiography", European Heart Journal (1991) 12, 473–480.
Proceedings of Computers in Cardiology, IEEE Press USA, 23 Sep. 1991, Venice Italy pp. 549–551, D. Eylon et al "A Ventricular Model with a 3-D Fractal Conduction Network".
S.H. Liu, "Formation and Anomalous Properties of Fractals", IEEE Engineering in Med. and Biology Magazine, Jun. 1992, pp. 28–39.
W. Deering et al, "Fractal Physiology", IEEE Engineering in Med. and Biology Magazine, Jun. 1992, pp. 40–46.

Ary L. Goldberger, "Fractal Mechanisms in the Electrophysiology of the Heart", IEEE Engineer, in Med. and Biology Magazine, Jun. 1992, pp. 47–52.
L.S. Liebovitch et al, "Ion Channel Kinetics", IEEE Engineering in Med. and Biology Magazine, Jun. 1992, pp. 53–56.
H.E. Schepers et al, "Four Methods", IEEE Engineering in Med. and Biology Magazine, Jun. 1992, pp. 57–71.
C.Fortin et al, "Fractal Dimension", IEEE Engineering in Med. and Biology Magazine, Jun. 1992, pp. 65–71.
Proceedings of Computers in Cardiology, IEEE Press USA, 19 Sep. 989, Israel, pp..137–140, O.Barenfeld et al "Simulation of Late Potentials Using a Computerized Three Dimensional Model of the Hearts Ventricles with Fractal Conduction System".
Annals of Biomedical Engineering, vol. 21, No.2,Mar. 1993, USA,pp. 125–134,O.Berenfeld et al "Modeling of the Hearts Ventricular Conduction System Using Fractal Geometry: Spectral Analysis of the QRS Complex",See p. 130,left col.,line 9–p. 134,right col.,line 6.
Medical & Biological Engineering & Computing, vol. 30, No. 5, Sep. 1992, UK, pp. 495–502, H. Bakardjian "Ventricular Beat Classifier Using Fractal No. Clustering", See p. 497, left col., line 24–p. 501, left col., line 23.

(List continued on next page.)

*Primary Examiner*—Scott M. Getzow
*Attorney, Agent, or Firm*—Cushman, Darby & Cushman IP Group of Pillsbury Madison & Sutro LLP

[57] ABSTRACT

A method and apparatus of analysing Ventricular Late Potential (VLP) including determining a parameter related to the complexity of the VLP as a parameter for clinical evaluation. The method may include computing the fractal dimension of the attractor for the VLP as a parameter for clinical evaluation. The method may include performing a spectral analysis producing an assessment based on a discrete Hartley transform (DHT) vector spectrum by summing amplitude components between $-f_1$ to $-f_2$ and $+f_2$ to $+f_1$, where $f_1$ is a number larger than $f_2$.

16 Claims, 9 Drawing Sheets

OTHER PUBLICATIONS

Joint Congress of the 16th International Conference on Medical and Biological Engineering, UK, vol. 31, 7 Jul. 1991, Kyoto, JP, pp. S137–S146, Escalona,O.J. et al "Fast and Reliable QRS Alignment Technique for High Frequency Analysis of Signal Averaged ECG" See p. S138, left col., line 25–p. S139, right col., line 16.

Proceeding of the Annual International Conference of the IEEE Engineering in Medicine and Biology Sociaty, IEEE Press USA, vol.1, 4 Nov. 1988, New Orleans USA, pp. 7–8, G.Harris "A Novel Approach to Pattern Recognition in Real Time Arrhythmia Detection".

$$L = \sum_{i=2}^{i=N} \{(X_f(i)-X_f(i-1))^2 + (Y_f(i)-Y_f(i-1))^2 + (Z_f(i)-Z_f(i-1))^2\}^{\frac{1}{2}}$$

Eq. 1

$$D_{ij} = \{(X_f(i)-X_f(j))^2 + (Y_f(i)-Y_f(j))^2 + (Z_f(i)-Z_f(j))^2\}^{\frac{1}{2}}$$

Eq. 2

$$\Delta = \begin{bmatrix} 0 & D_{12} & D_{13} & . & D_{1i} & . & D_{1N} \\ D_{21} & 0 & D_{23} & . & D_{2i} & . & D_{2N} \\ D_{31} & D_{32} & 0 & . & D_{3i} & . & D_{3N} \\ . & . & . & . & . & . & . \\ D_{j1} & D_{j2} & D_{j3} & . & 0 & . & D_{jN} \\ . & . & . & . & . & . & . \\ D_{N1} & D_{N2} & D_{N3} & . & D_{Ni} & . & 0 \end{bmatrix}$$

$\delta = 1.1214$

Fig. 4

$\delta = 1.4373$

Fig. 5

| P# (Group 1P) | RMS40 (μV) | LAS40 (ms) | fQRSd (ms) | δ |
|---|---|---|---|---|
| 1 | 23 | 37 | 115 | 1.2428 |
| 2 | 28 | 24 | 103 | 1.1908 |
| 3 | 40 | 34 | 87 | 1.2675 |
| 4 | 19 | 44 | 108 | 1.3093 |
| 5 | 46 | 23 | 105 | 1.0892 |
| 6 | 20 | 37 | 95 | 1.2675 |
| 7 | 60 | 28 | 90 | 1.1716 |
| 8 | 18 | 39 | 98 | 1.2932 |
| 9 | 25 | 35 | 100 | 1.2659 |
| 10 | 21 | 24 | 104 | 1.1988 |
| 11 | 59 | 27 | 94 | 1.2526 |
| 12 | 19 | 35 | 99 | 1.3111 |
| 13 | 42 | 24 | 94 | 1.1954 |
| 14 | 88 | 24 | 91 | 1.1630 |
| 15 | 80 | 24 | 94 | 1.1214 |
| 16 | 21 | 31 | 111 | 1.2967 |
| 17 | 19 | 44 | 108 | 1.3032 |
| 18 | 14 | 39 | 100 | 1.2192 |
| 19 | 39 | 23 | 95 | 1.1304 |
| 20 | 33 | 29 | 89 | 1.2774 |
| 21 | 12 | 40 | 115 | 1.2619 |
| 22 | 21 | 35 | 117 | 1.1693 |
| 23 | 32 | 32 | 104 | 1.2385 |
| 24 | 26 | 37 | 94 | 1.2636 |

Fig. 6a

| P# (Group 1P) | RMS40 (μV) | LAS40 (ms) | fQRSd (ms) | δ |
|---|---|---|---|---|
| 25 | 49 | 28 | 95 | 1.2601 |
| 26 | 36 | 21 | 97 | 1.2572 |
| 27 | 21 | 34 | 102 | 1.2451 |
| 28 | 36 | 20 | 92 | 1.1154 |
| 29 | 20 | 34 | 104 | 1.1633 |
| 30 | 31 | 27 | 92 | 1.1436 |
| 31 | 44 | 38 | 101 | 1.1923 |
| 32 | 46 | 24 | 100 | 1.1892 |
| 33 | 72 | 17 | 71 | 1.1494 |
| 34 | 42 | 19 | 96 | 1.1325 |
| 35 | 129 | 15 | 86 | 1.1281 |
| 36 | 95 | 18 | 83 | 1.1002 |
| 37 | 68 | 23 | 91 | 1.2175 |
| 38 | 74 | 21 | 89 | 1.2236 |
| 39 | 58 | 23 | 90 | 1.2132 |
| 40 | 21 | 32 | 113 | 1.1399 |
| 41 | 22 | 38 | 109 | 1.2749 |
| 42 | 22 | 38 | 99 | 1.2954 |
| 43 | 20 | 35 | 103 | 1.1873 |
| 44 | 46 | 23 | 90 | 1.1890 |
| 45 | 19 | 33 | 98 | 1.2412 |
| MV | 39.47 | 29.56 | 98.02 | 1.2124 |
| SD | 25.02 | 7.63 | 9.22 | 0.0622 |

Fig. 6b

| P # (Group 2P) | RMS40 (µV) | LAS40 (ms) | fQRSd (ms) | δ |
|---|---|---|---|---|
| 1 | 8 | 53 | 170 | 1.4095 |
| 2 | 20 | 36 | 119 | 1.2802 |
| 3 | 17 | 41 | 112 | 1.3841 |
| 4 | 3 | 77 | 161 | 1.3758 |
| 5 | 19 | 40 | 110 | 1.3212 |
| 6 | 12 | 44 | 104 | 1.3586 |
| 7 | 9 | 56 | 105 | 1.4350 |
| 8 | 20 | 59 | 155 | 1.4862 |
| 9 | 16 | 43 | 114 | 1.3154 |
| 10 | 14 | 45 | 113 | 1.4022 |
| 11 | 7 | 47 | 127 | 1.3029 |
| 12 | 17 | 39 | 109 | 1.3600 |
| 13 | 10 | 48 | 108 | 1.3224 |
| 14 | 12 | 58 | 146 | 1.3914 |
| 15 | 12 | 60 | 124 | 1.4248 |
| 16 | 13 | 56 | 130 | 1.4315 |
| 17 | 16 | 54 | 125 | 1.3694 |
| 18 | 15 | 39 | 100 | 1.3163 |
| 19 | 10 | 46 | 122 | 1.4139 |
| MV | 13.21 | 49.53 | 123.90 | 1.3737 |
| SD | 4.72 | 10.07 | 20.25 | 0.0541 |

Fig. 7

| | PV | SV |
|---|---|---|
| RMS40 | 4.521 | 6.761 |
| LAS40 | -8.681 | -7.757 |
| fQRSd | -7.060 | -5.340 |
| δ | -9.821 | -10.400 |

ANALYSIS OF HEART WAVEFORMS

This application claims benefit of international application PCT/GB94/01117, filed May 20, 1994.

BACKGROUND OF THE INVENTION

1. Field of the Invention

This invention relates to the analysis of heart waveforms and, more particularly, to the heart waveform represented by the measurement known as the Ventricular Late Potential (VLP).

2. Description of the Related Art

It is known to apply temporal fractals to the study of cardiac rhythm (See, Goldberger et al., Experimental 1988; 44:983–987 and other citations in IEEE Engineering in Medicine and Biology, 1992, June p52). Goldberger suggests that disease states may lead to a loss of the physiological complexity of measurements and therefore to greater regularity, not a greater irregularity, in the measured phenomenon.

SUMMARY OF THE INVENTION

It is an object of the invention to provide, from an analysis of ventricular late potential measurements, an indication of a parameter significant for clinical evaluation.

The invention provides a method of analysing Ventricular Late Potential (VLP), including determining a parameter related to the complexity of the VLP as a parameter for clinical evaluation.

According to the invention, there is provided a method of analysing Ventricular Late Potential (VLP) including computing the fractal dimension of the attractor for the VLP as a parameter for clinical evaluation.

Preferably the VLP attractor is in three dimensional voltage space, the voltage being ECG measurements.

The geometrical realization of the attractor, which need not be carried out to perform the invention, may be considered as a path in phase space defined by ECG voltages in three orthogonal directions.

The method may include an approximation to the fractal dimension of the attractor as the quotient of log(L)/log(DD), where L is the total length of the attractor and DD is the spheric extent diameter of the attractor. The approximation may be produced by the application of an algorithm, conveniently in the form of a flow chart.

The method may include assessing the ECG signals to define VLP onset and offset points. The assessment of the ECG signals may include signal-averaging and high-pass filtering and the taking of the absolute value of the filtered output.

In one assessment, the onset is defined as the vector magnitude combination exceeding a chosen mean or peak voltage. This may be 40 micro volts mean or 48 microvolts peak (mean±20%). In one assessment the offset is defined as the mean voltage exceeding the mean noise level plus three times the standard deviation of the noise sample.

A fractal dimension in excess of 1.30 may be selected as the value indicating a risk of sudden cardiac death positive (SCD+) condition. The fractal dimension may be provided as a display or other output.

To optimise ECG signal collection, a particular form of amplifier may be employed including three operational amplifiers with a high gain in an early front end stage to minimise noise over a controlled bandwidth, which may be 0.1 to 1200 Hz, and low crosstalk, which may be below −90dB.

Spectral analysis of VLP may be performed to produce an assessment based on a discrete Hartley transform (DHT) vector spectrum by summing amplitude components between $-f_1$ to $-f_2$ and $+f_2$ to $+f_1$ where $f_1$ is a number larger than $f_2$. A value in the upper part of the range of an individual assessment for a group including persons believed healthy and persons believed to be SCD+ indicates risk of SCD+ and provides a parameter for clinical evaluation.

The basic fractal techniques are now becoming known from the works of several authors including B. B. Mandelbrodt, J. Feder and D. Stauffer and H. E. Stanley to which reference is directed for these techniques.

BRIEF DESCRIPTION OF THE DRAWINGS

Embodiments of the invention will now be described with reference to the accompanying drawings, in which.

DETAILED DESCRIPTION OF THE PREFERRED EXEMPLARY EMBODIMENT

Figure 1:
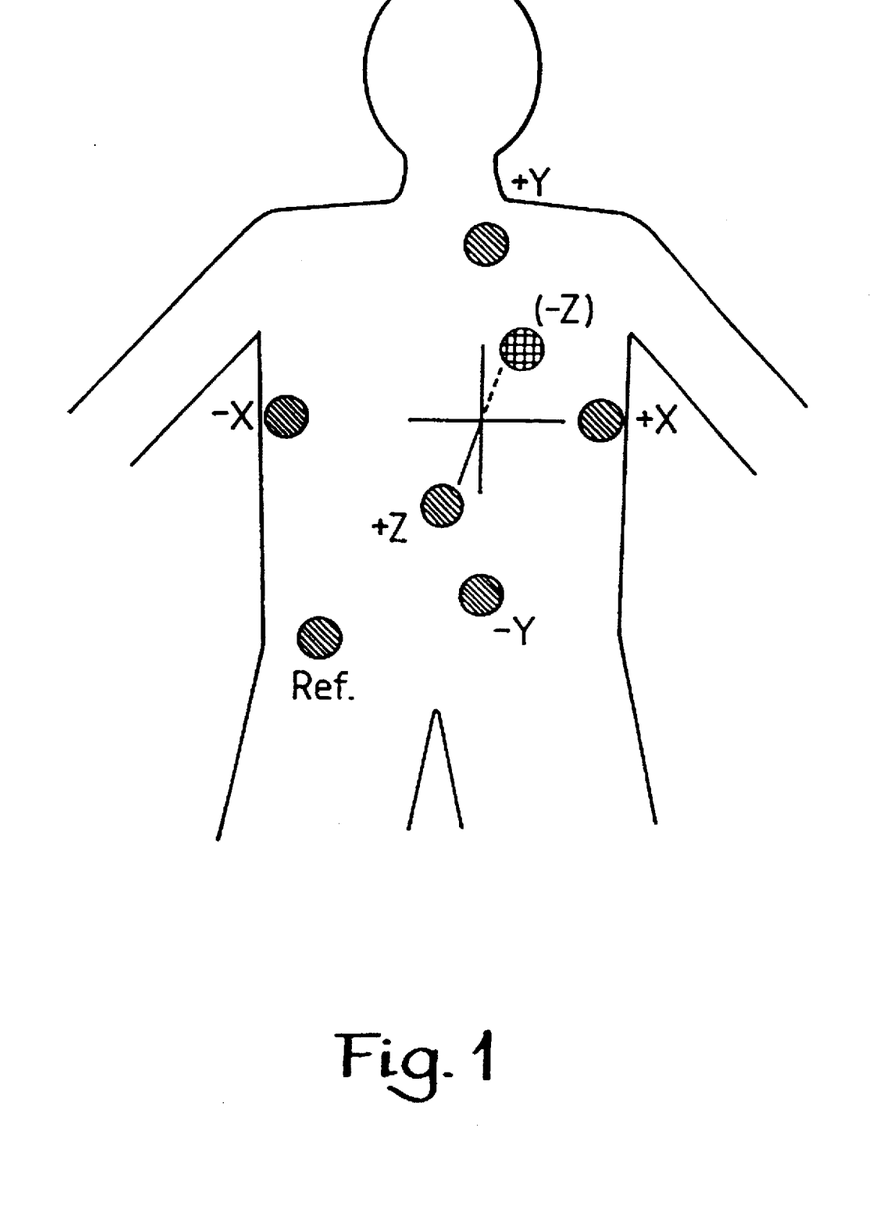
FIG. 1 is a diagram of electrode positions on the front, sides and back of a human torso.

FIG. 1 shows the position of electrodes in the conventional bipolar orthogonal XYZ lead system. The pairs of electrodes (+X, −X) (+Y, −Y) and (+Z, −Z) each relate to an orthogonal axis, X, Y and Z respectively. Electrode −Z is on the back of the torso, electrode +Z on the front, electrodes +X and −X are on the sides of the torso and electrodes +Y and −Y at the top and bottom, respectively, of the torso. A reference lead electrode (REF) is also used. Standard, pre-gelled, disposable ECG electrodes are used. For analysis purposes the three channels (X, Y and Z) are recorded simultaneously in digital form. An example of such an arrangement is disclosed in U.S. Pat. No. 4,478,223.

Figure 11:
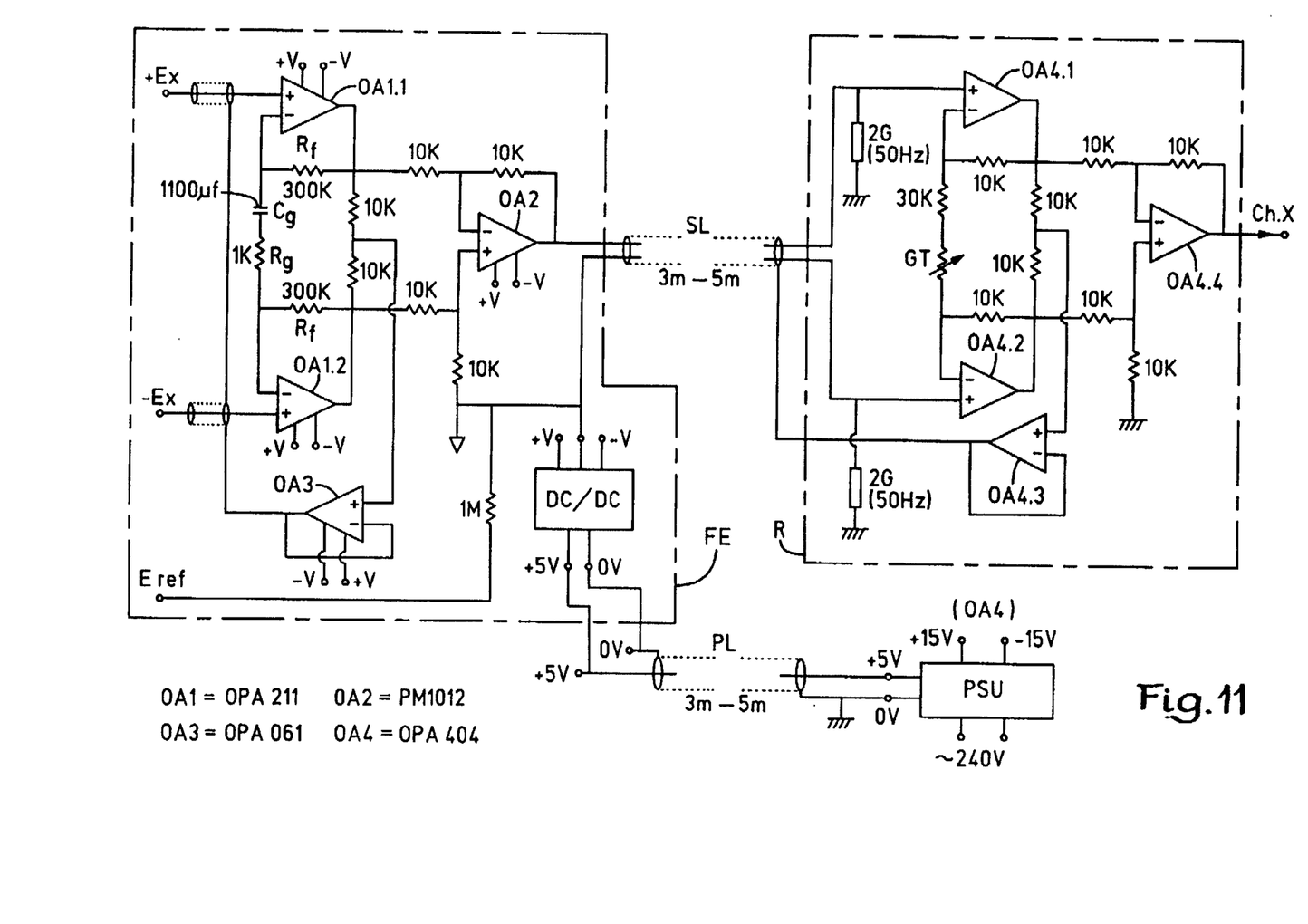
FIG. 11 shows a circuit diagram of an amplifier for ECG signals.

In one arrangement, according to the invention, a low noise, high gain, three channel ECG amplifier having a frequency band width from 0.1 to 1200 Hz and cross talk below −90dB is used for conditioning the ECG signals from electrode pairs. (FIG. 11 shows such an amplifier.) Each channel is digitised at 4000 Hz with 16-bit resolution. Each ECG digital recording is 7 or 11 megabytes in length, depending on the basic heart rate and the background noise during the recording. Gain for each channel can be set independently at between 1000 and 20000 and the values noted for the later off-line processing. A back-up record is made on a tape streamer.

Off-line signal processing of each ECG is as follows. Signal averaging is performed until the rms noise level during diastole is less than 0.3 microvolts. Standard deviation of trigger jitter is estimated to be less than 0.2 milliseconds, provided that the rms noise level in the raw ECG is less than 40 microvolts. The Single Fiducial Point (SFP) alignment technique is used (See Escalona O. J. et al., A fast and reliable beat alignment technique, Med. Bio. Eng & Comp., 29, Supp, 1991). Each beat is cross correlated with a template beat and was rejected for averaging if it is an ectopic beat. Excessively noisy beats with rms noise greater than 40 microvolts are also rejected. High-pass filtering is performed digitally on each signal averaged lead. A 40 Hz bidirectional 4th order Butterworth high-pass filter is used according to the standard method (See Breithardt. G. et al. Standards for analysing of ventricular late potentials, Eur. Heart J. (1991) 12, 473–480) to produce signals $X_f$, $Y_f$ and $Z_f$.

Analysis in accordance with the invention is carried out on these filtered signals, after taking absolute values of the filter output. Ventricular late potentials (VLP) start and end points are defined as follows. The end point ($VLP_{off}$) for each signal is defined as the mid-point of a 5 milliseconds segment shifted along the ST segments towards the QRS complex in one millisecond steps until the mean voltage exceeds the mean noise level plus three times the standard deviation of noise sample (see Breithardt, above). The terms QRS and ST are those regularly used for electrocardiograms. The largest value of $VLP_{off}$ among the three is chosen as the end point ($t_E$=largest $VLP_{off}$).

The starting time of the $VLP_{(t_o)}$ is defined on the vector magnitude combination of the three filtered orthogonal leads $(X_f^2+Y_f^2+Z_f^2)^{1/2}$, as the end-point ("right-hand" end) of a 5 milliseconds segment shifted from $t_E$ into the QRS complex in one millisecond steps until its mean voltage exceeds 40 microvolts or has a peak value of 48 microvolts (i.e. 40 microvolts+20%) to accommodate very brief peaking of the VLP vector magnitude.

All the VLP amplitude values are expressed in microvolt units and the VLP attractor is traced in the three dimensional voltage space with the X, Y, Z leads as the orthogonal axis (µV3D space). (See FIGS. 4 and 5). Each point of the trace corresponds to a certain time between $t_o$ and $t_E$ and has as co-ordinates the values of VLP amplitude of each corresponding filtered lead (X, Y, Z) at that particular time.

An important feature of the invention is the estimated fractal dimension (δ) of the VLP attractor. A technique for this estimation is described below and uses the following expression:

$$\delta = \log(L)/\log(DD)$$

where L is the total length of the trajectory of the attractor and DD is the spheric extent (maximum diameter) encompassing the attractor (both measured in microvolts).

The attractor trajectory (see FIGS. 4 and 5) is a discrete 3D curve in which points correspond to the sampling interval in each ECG lead recording (in one example 0.25 milliseconds).

The total length L is the sum of all the step distances between adjacent points in the curve. If there are N time steps each of 0.25 milliseconds between $t_o$ and $t_E$ then L is given by Equation 1 in FIG. 3.

The maximum diameter DD is obtained as follows. For every one of the N points on the curve the values of distance to each other (N-1) points is calculated. The absolute maximum of all the calculated distances is evaluated. The distance Dij between an ith and a jth point in the attractor curve is given by Equation 2 in FIG. 3.

Figure 3:
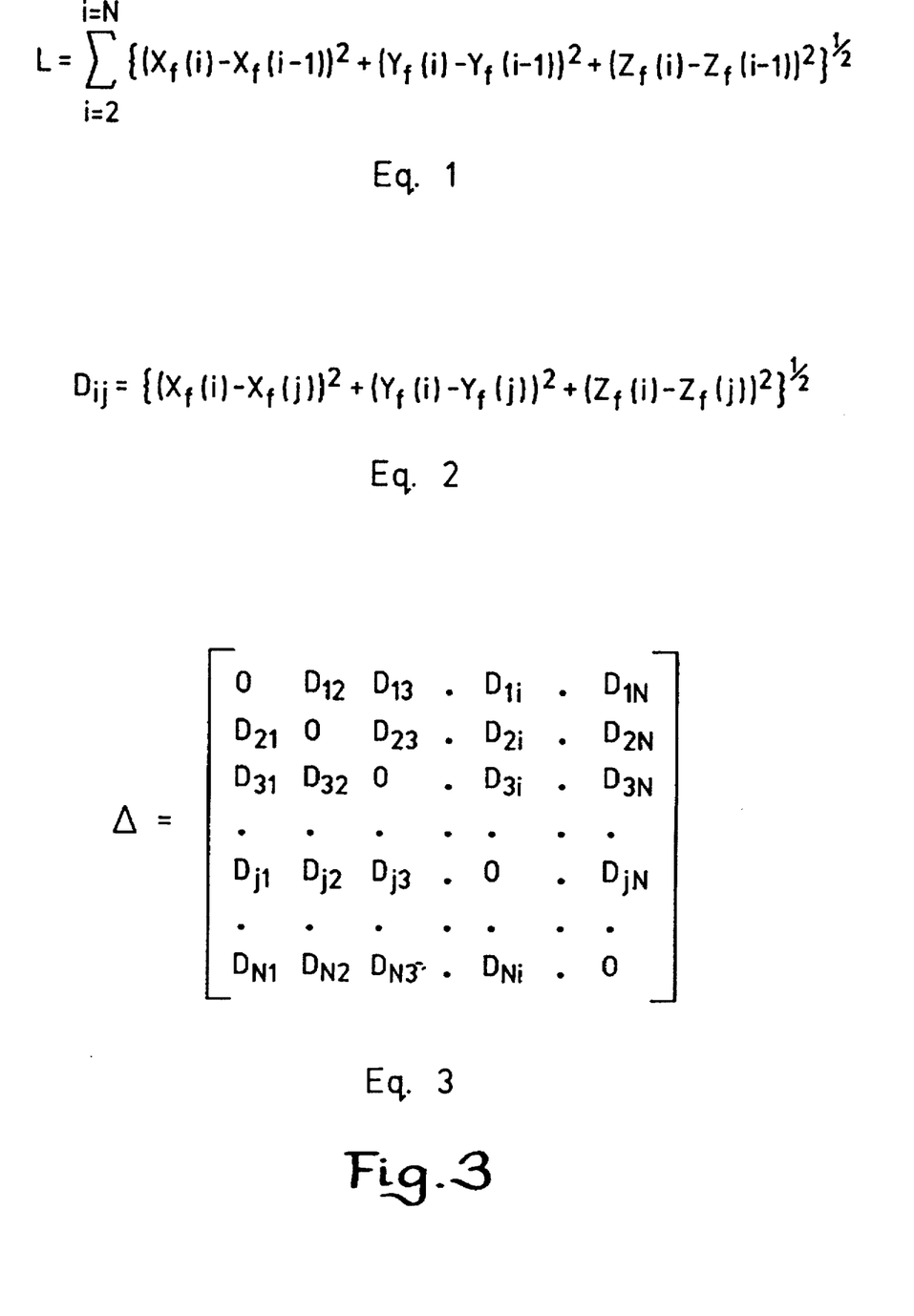
FIG. 3 shows equations useful in practicing the invention.

The matrix representation of all possible Dij elements, namely the distance matrix Δ, is equation 3 in FIG. 3.

In theory, the determination of DD requires the computation of N*(N-I) distances, i.e. computation of equation (3) for N*(N-1) times. N has been found to be as large as 320 in some abnormal subjects (VLP duration of 80 milliseconds), and thus, $10^4$ computations would be needed for DD.

However, Dij=Dji, i.e. Δ is symmetrical. Accordingly, the number of calculated distances can be halved if the process for DD is carried out on only the distance elements in the upper triangle of Δ. This is expressed as follows:

$$DD = \text{Max.} \left| \left| Dij \Big|_{i=1+j}^{i=N} \right|_{j=1}^{j=N-1} \right| \quad \text{Eq (4)}$$

Figure 2:
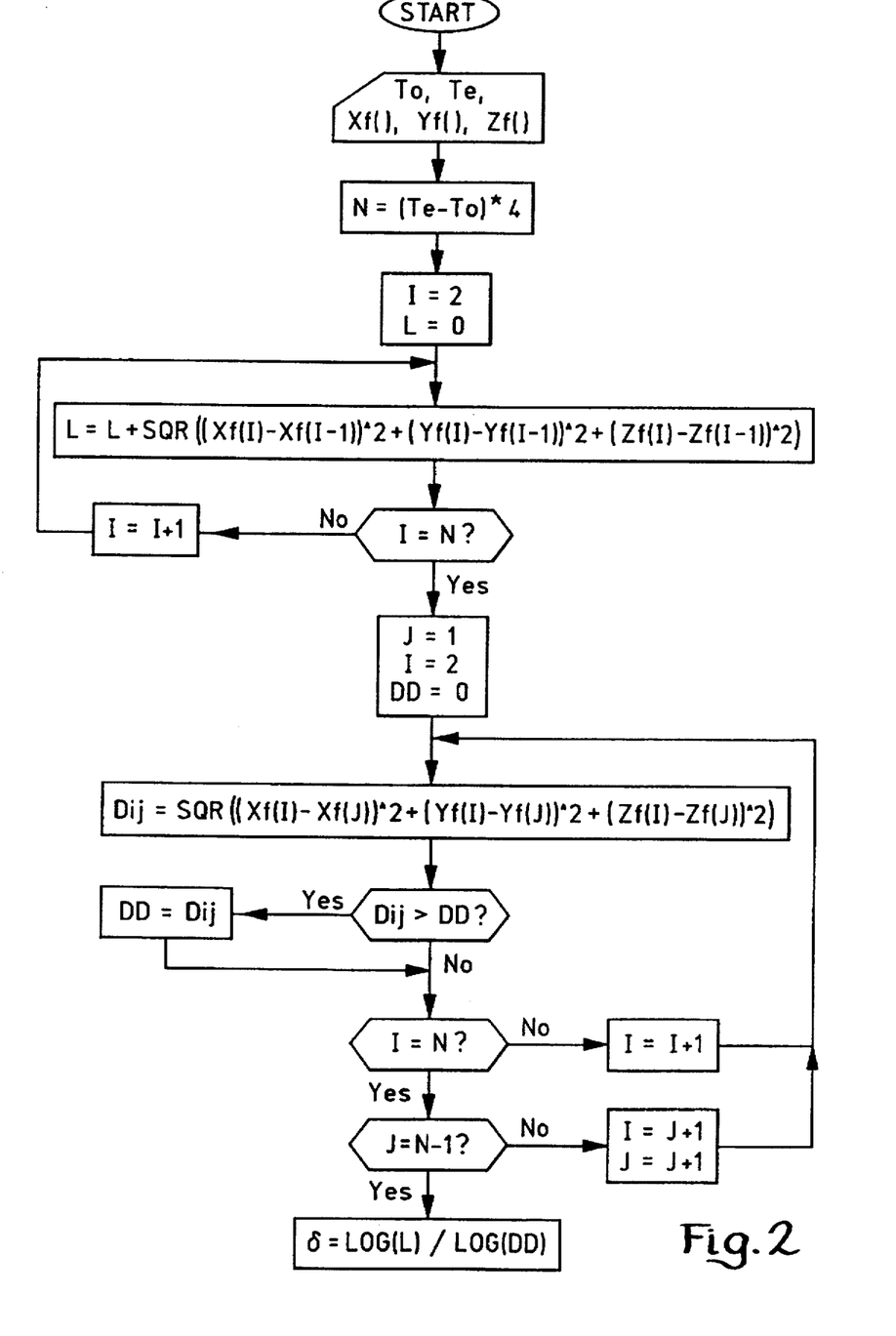
FIG. 2 is a flow chart for an algorithm for computing the fractal dimension of an attractor.

FIG. 2 shows the flow chart for computing δ as described above.

Figure 4:
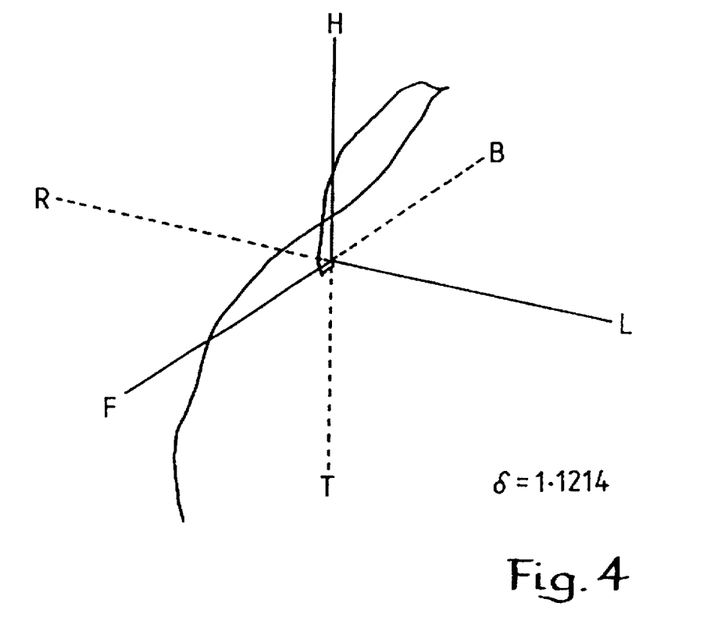
FIGS. 4 and 5 are each the representation of an attractor.
Figure 5:
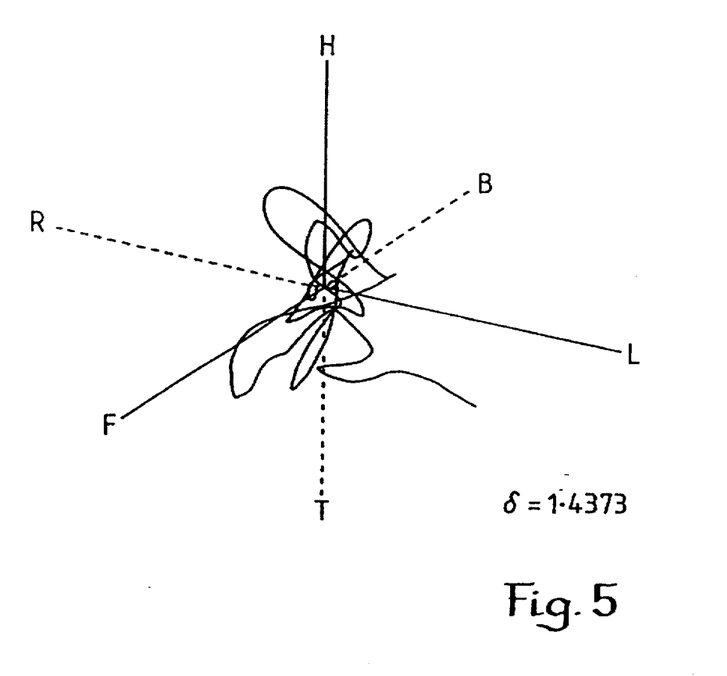

FIGS. 4 and 5 show in convenient projections VLP attractors actually measured in accordance with the invention. The values plotted are up to some tens of microvolts. The value of δ calculated as above is shown on each Figure. Relating these Figures to FIG. 1 the H/T axis (head/feet) corresponds to the +Y/-Y electrodes, the R/L axis (right side/left side) corresponds to the -X/+X electrodes and the F/B axis (torso front/torso back) corresponds to the +Z/-Z electrodes.

FIG. 4 is the VLP attractor for a person believed to be healthy (δ=1.1214) and FIG. 5 the VLP attractor for a person believed to be SCD+ (that is at risk of Sudden Cardiac Death) (δ=1.4373) on the accepted Late Potential prediction criteria (See, Breithardt et al. above).

It is widely accepted that certain directly observable Late Potential features are a useful predictor of SCD+ for a person after a myocardial infraction (MI). Breithardt et al. set these out as three criteria:

(1) fQRSd longer than 114 milliseconds
(2) RMS40 less than 20 microvolts
(3) LAS40 longer than 38 milliseconds (Here fQRSd is the filtered QRS duration, RMS40 is the root mean square amplitude of the terminal 40 millisecond and LAS40 the duration of low amplitude signals (below 40 microvolts) in the vector magnitude QRS complex using 40 Hz high-pass bidirectional filtering.) When at least two of the three criteria are satisfied a person should be considered to be late potential positive (LP+) and if post –MI considered to be SCD+.

Figure 6A:
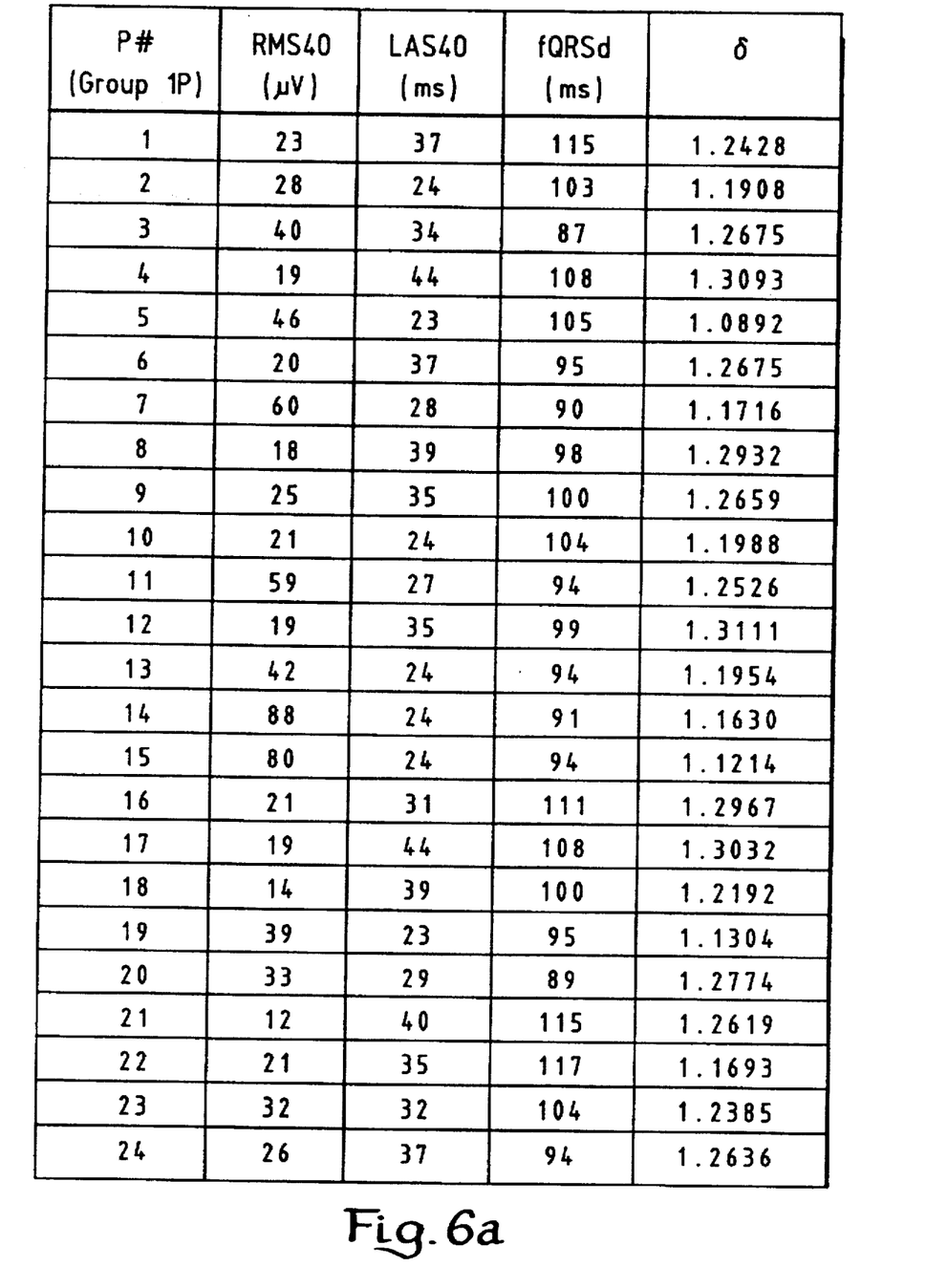
FIGS. 6a, 6b, 7 and 8 are tables of results of measurements according to the invention, FIGS. 9 and 10 each show a DHT vector spectrum.
Figure 6B:
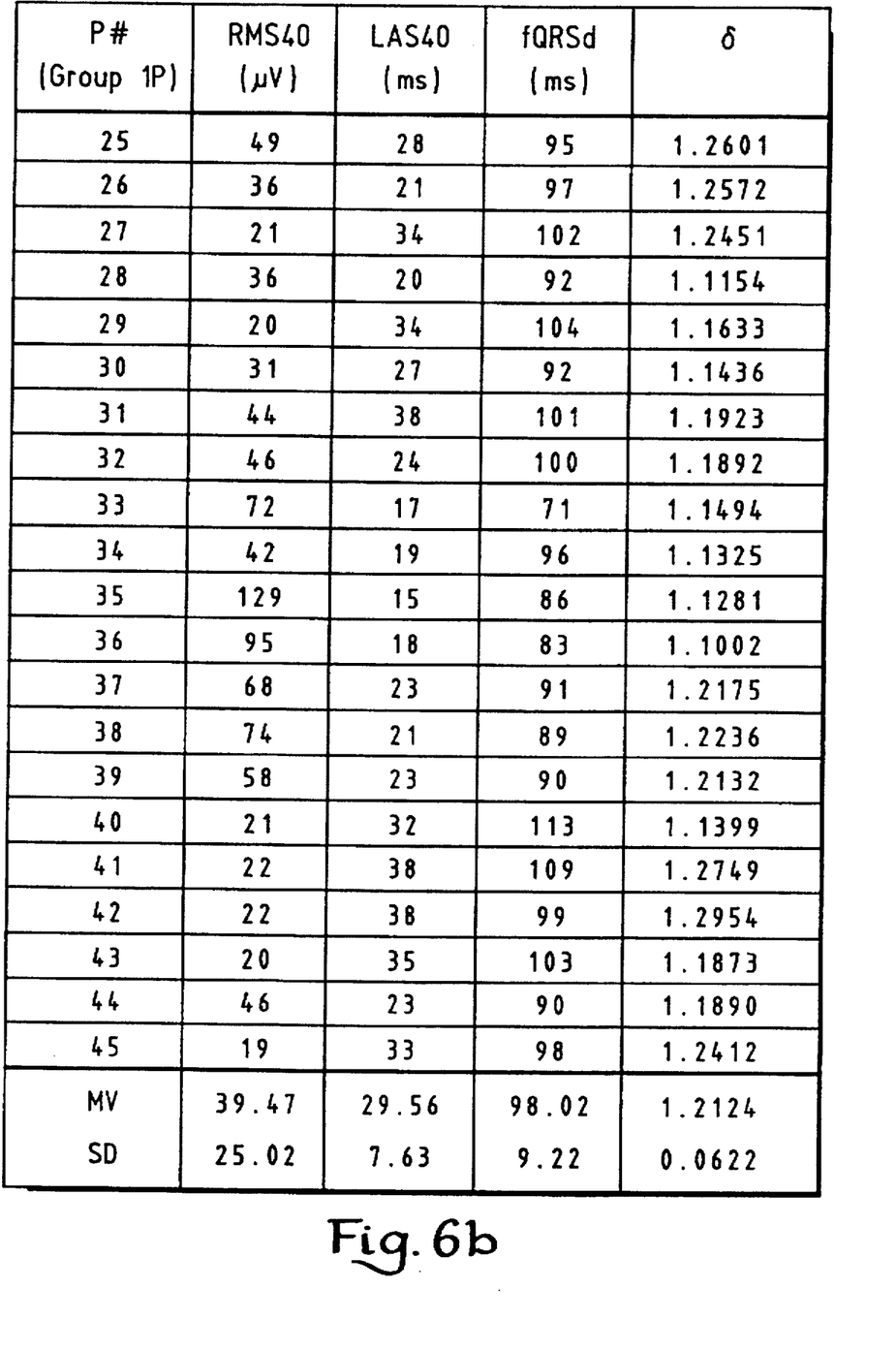
Figure 7:
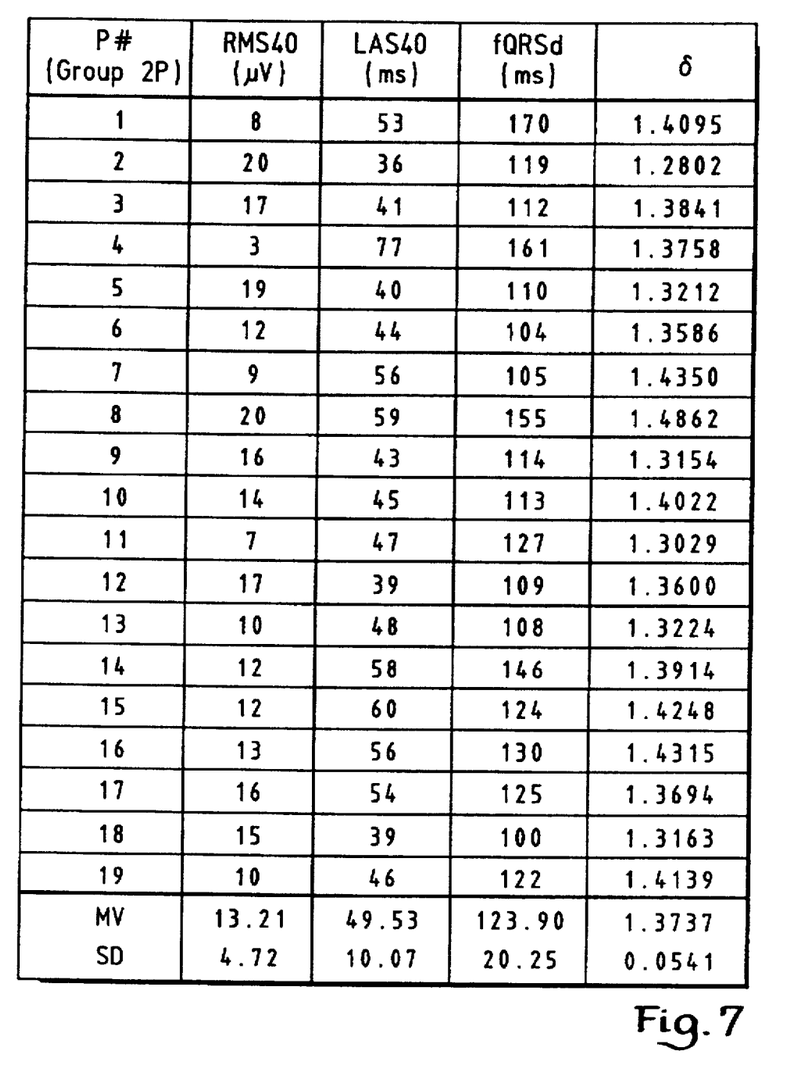

FIGS. 6a and 6b show results for a group of 45 persons believed healthy (regardless of whether they presented as normal VLP activity or not, mean age 38±8 years). FIG. 7 shows results for a group of 19 persons believed post-MI SCD+ and at risk (according to their medical history and having abnormal VLP activity according to the above standard analysis, mean age 58±12 years). Column P# distinguishes the persons in each group, other columns are the above three conventional criteria while δ is the fractal dimension calculated according to the invention. The Figures include the mean value (MV) and standard deviation (SD).

Figure 8:
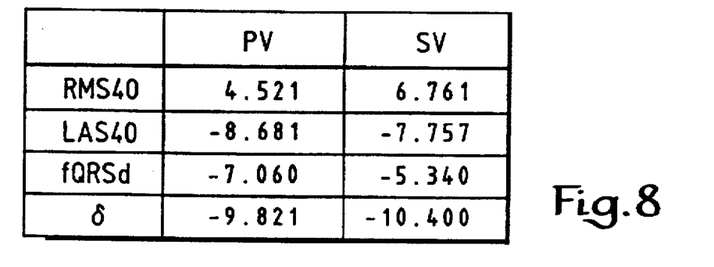

FIG. 8 shows the pooled variance (PV) and separated variance (SV) for a statistical Student t-test on the criteria results for the group In FIGS. 6a and 6b against the criteria results for the group In FIG. 7.

The conventional criteria (RMS40, LAS40 and fQRSd) referred to above are from the time-domain of the electrode waveforms and depend on the algorithm used for detecting the onset and offset points of the filtered QRS complex. (This algorithm implements a standard definition given in Breithardt for the onset and offset points of the filtered QRS complex.) When micropotentials (less than 5 microvolts) are long delayed and with slow termination the algorithm Is expected to err systematically, especially under noisy conditions.

By using a parameter defined in the 3-D micro voltage space instead of the 2D voltage-time plane, significant advantages are achieved. In the 3-D space, curved behaviour depends only on voltage changes. A consequence of this is that small voltage changes (less than 5 microvolts) in a relatively long period of time can yield only small curve changes. Large curve fluctuations or changes would increase the complexity of the curve and consequently its fractal dimension. The fractal dimension method requires the use of the $VLP_{off}$ detection algorithm but the value of w is less critically dependent on the performance of the algorithm. The voltage range of ±40 microvolts is specified by the definition of VLP. For smaller ranges, say ±5 microvolts, the computed values of w would have been different, more sensitive to sub-microvolt late potential activity and more susceptible to noise after signal averaging.

Values of w ranged between 1 and 1.5 for the technique described above. From the definition of the Hausdorff-Besicovitch dimension w can not be greater than 3. The value of w is close to 1 when the VLP attractor converges from a +40 or a −40 microvolt potential (at the VLP starting point) to the origin ($VLP_{off}$) in a practically straight line trajectory. In the case of subjects believed healthy there is a very sharp termination of the QRS complex. The contrast between a VLP attractor trajectory with a w value closer to 1 (w=1.1214) and one with a w value closer to 1.5 (w=1.4373) is seen from FIGS. 4 and 5.

Apparatus to perform the invention can be arranged in any convenient form. One arrangement is a specific electronic unit to which suitable signals are supplied and which carries out the attractor fractal dimension computation with suitably arranged electronic calculating devices to provide an indication on the unit or an associated display of the calculated fractal dimension for the supplied signals. The ECG signal amplifiers described herein may be associated with or incorporated in the apparatus if required.

The size of the sample shown in the tables of results is relatively small but is sufficient for an assessment of the clinical significance of 6 as an indicator (discriminator) of SCD+ in patients. Further a threshold value for δ can be identified above by which a post-MI patient can be classified as SCD+. A suggested basis for this value ($δ_{SCD+}$) is the mean value of δ in the group of persons believed healthy plus two times the standard deviation (FIG. 6). In this specific example this value is 1.337. An alternative suggested basis for such a threshold value Is the mean value of δ for the group of persons believed healthy (1.2124) and δ for the group of persons believed to be SCD+ (1.3737), this value of $δ_{SCD+}$ is 1.293. The justification for this basis is the closeness of the standard deviation of δ for the two groups shown, viz 0.062 and 0.054. A value of $δ_{SCD+}$ of 1.30 produces three false positives in the "healthy" group and one false negative in the "SCD+" group.

A canine model study provided more controlled conditions than possible with human patients. (For example In the FIG. 6 "healthy" group there are some LP+ conditions while the post-MI group of FIG. 7 includes cases which could have become completely healed). This model study yielded smaller and closer deviations for the "healthy" and SCD+ groups (0.0411 and 0.0468 respectively). The smaller deviations reflected the more controlled conditions of the model study.

The above techniques show that it is likely that the fractal dimension of the VLP attractor in post-MI, SCD+ subjects is significantly higher than in "healthy" subjects, to the degree of 1 part In 1000 that this is not the case. Further, compared to the QRS offset detection method, the above technique has a lower vulnerability to errors made by the algorithem and therefore offers better reliability in automated use. The complexity in $_µV3D$ space can be interpreted as a measure of chaotic behaviour that could trigger a catastrophic arrhythimic episode.

Figure 9:
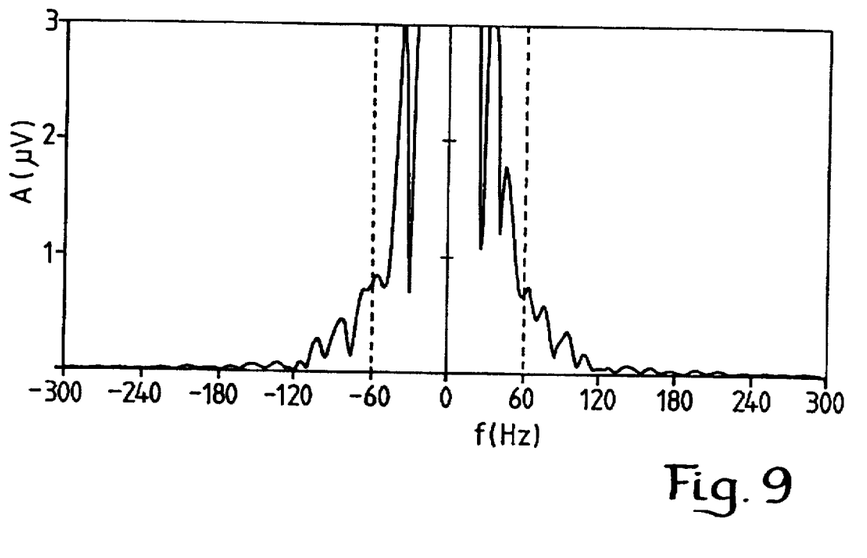
Figure 10:
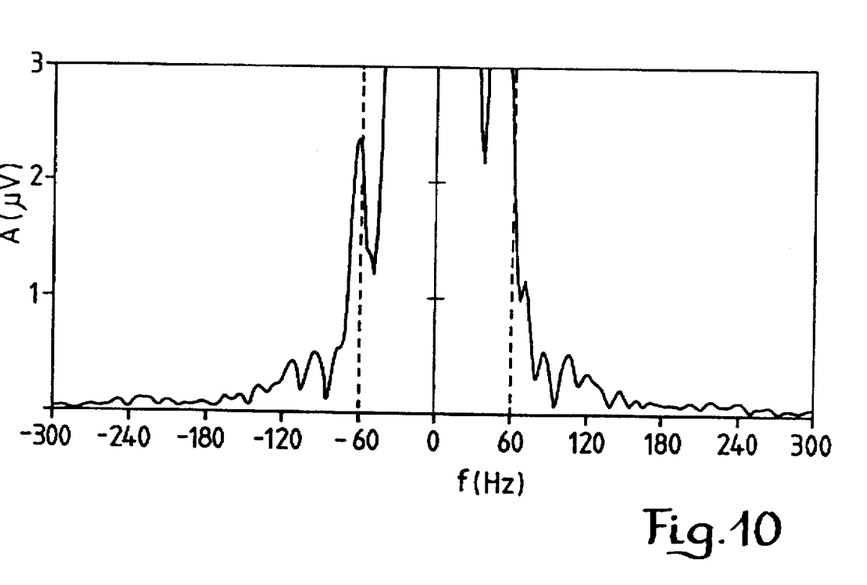

FIGS. 9 and 10 show the results of another technique according to an aspect of the invention for assessing VLP in which a discrete Hartley transform vector spectrum is used. The spectrum amplitude components (A) are summed in two frequency ranges, $-f_1$ to $-f_2$ and $+f_2$ to $+f_1$ where $f_1$ is a number larger than $f_2$, for example −300 Hz to −60 Hz and +60 Hz to +300 Hz. FIG. 9 is an assessment for a person believed healthy and FIG. 10 for a person believed SCD+. A higher value in the range of summed components for healthy and SCD+ persons indicates SCD+ risk. The higher value of summed components is believed to relate to increased complexity of the VLP and thus to SCD and condition.

FIG. 11 is the circuit diagram of an ECG amplifier to enhance signal collection and useful in the practice of the present invention. A three-operational amplifier front end FE has high early gain to minimise noise over a controlled bandwidth, for example 0.1 to 1200 Hz and low crosstalk, below −90 dB. The amplifier for only one electrode pair, for example the x axis $+E_x$ and $-E_x$ supplying one channel X, is shown for simplicity. The gain/bandwidth control elements $C_g$ and $R_g$ are typically 10 mF to 1500 mF and 10 KL to 100 L respectively. The values chosen for $C_g$ and $R_g$ set $f_c$, the 3 dB cut-off frequency, and a typical value for this in the above techniques is 0.14 Hz. The differential gain is determined by $R_f$ and $R_g$ and the noise is related to the differential gain. Values of $R_f$ above 1 ML increase the noise significantly. A value of $R_f$ around 300 kL is a good compromise with $C_g$ at 1100 mF and $R_g$ at 1 KL. This enables the use of the minimum number of high-quality operational amplifiers while achieving high gain at low noise and resistance to interference from e.g. CRT scan frequencies and power frequencies such as 50 Hz, 60 Hz and their harmonics. The front end (FE) is connected to a receiver (R) by a signal line SL of up to three to five meters. The receiver also includes a regulated power supply (PSU) which supplies DC power to the receiver and via a similar length of power line PL, the front end where a DC/DC convertor provides appropriate voltages. The receiver channel output, for example Ch X, is connected to a high pass filter. The receiver gain is adjustable with a gain trim GT.

The rest of the components and values are shown in FIG. 11. Screened and balanced cables are used as indicated. Constructional details appropriate to the high-gain, low-noise requirements will be apparent to those skilled in the art. Clearly variations are possible for specific components and applications.

Other equipment than that specifically described may be used to carry out the techniques of the invention, having regard to the performance requirement set out above.

I claim:

1. A method of analyzing Ventricular Late Potential (VLP) comprising:
   measuring electrocardiogram signals of a patient in at least three dimensions and deriving three dimensional VLP values from the electrocardiogram signals;
   determining an VLP onset point and a VLP offset point based on the three dimensional VLP values;
   deriving an attractor for the VLP in at least a three dimensional voltage space from the VLP values between the VLP onset point and the VLP offset point;
   estimating a fractal dimension of the VLP attractor from a quotient of Log(L)/Log(DD), where L is a total length of the VLP attractor between the VLP onset point and the VLP offset point, and DD is a spherical extent of the VLP attractor; and analyzing a condition of a patient based on the estimate fractal dimension.

2. A method according to claim 1 including assessing the ECG signals by signal-averaging and high-pass filtering to produce a filtered output and taking an absolute value of the filtered output.

3. A method according to claim 1 including defining the VLP onset point as a vector magnitude combination exceeding one of a predetermined mean and a predetermined peak voltage.

4. A method according to claim 3 wherein the vector magnitude defining the VLP onset point is 40 micro volts mean and 48 microvolts peak (mean±20%).

5. A method according to claim 1 including defining the VLP offset point as a mean voltage exceeding a mean noise level plus three times a standard deviation of a noise sample.

6. A method according to claim 1 including providing a specific output on computing a fractal dimension in excess of a value selected as a value indicating a risk of a sudden cardiac death positive (SCD+) condition.

7. A method according to claim 6 wherein the value selected as being a value indicating a risk of a SCD+ condition is in excess of 1.30.

8. A method according to claim 1 including collecting ECG signal with an amplifier defined by three operational amplifiers with a high gain in an early front end stage arranged to minimize noise over a controlled bandwidth of 0.1 to 1200 Hz and reduce crosstalk below −90 dB.

9. A method according to claim 1 including producing an approximation of the fractal dimension of the VLP attractor by the application of an algorithm in the form of a flow chart.

10. A method of analyzing Ventricular Late Potential comprising:

measuring electrocardiogram signals of a patient in at least three dimensions and deriving three dimensional VLP values from the electrocardiogram signals;

performing a discrete Hartley transform (DHT) of the electrocardiogram signals to obtain a vector spectrum of amplitude components;

summing amplitude components between $-f_1$ to $-f_2$ and $+f_2$ to $+f_1$, where $f_1$ is a number larger than $f_2$, of the vector spectrum obtained by performing the discrete Hartley transform; and assessing a condition of a patient based on the summation of amplitude components of the vector spectrum of the discrete Hartley transform.

11. A method according to claim 10 including identifying for a group of people including persons believed healthy and persons believed to be SCD+, a value in an upper part of a range of individual assessments as indicating risk of a SCD+ condition.

12. An apparatus to analyze Ventricular Late Potential (VLP) comprising:

means for receiving electrocardiogram signals from a patient and for deriving three dimensional VLP values from the electrocardiogram signals;

means for determining VLP onset points and VLP offset points based on the three dimensional VLP values;

means for deriving an attractor for the VLP values in at least a three dimensional voltage space from the VLP values between the VLP onset point and the VLP offset point; and means for estimating a fractal dimension of the VLP attractor from a quotient of Log(L)/Log(DD), where L is a total length of the VLP attractor between the VLP onset point and the VLP offset point, and DD is a spherical extent of the VLP attractor, so that the estimated fractal dimension can be used to analyze the condition of the patient.

13. An apparatus according to claim 12 wherein said means for receiving the electrocardiogram signals including signal channel amplifiers comprising three operational amplifiers with a high gain in a front end stage over a controlled bandwidth and reduced crosstalk.

14. An apparatus according to claim 13 wherein the bandwidth is 0.1 Hz to 1200 Hz and the crosstalk is below −90 dB.

15. Apparatus according to claim 12 wherein said receiving means includes electrocardiogram signal-averaging means and high-pass filtering means to produce a filtered output and means to deliver an absolute value of the filtered output.

16. Apparatus according to claim 12 further comprising means for providing an appropriate output indication on a determination of a parameter value in excess of, or below, a selected value.

* * * * *